(12) United States Patent
Schnarr (10) Patent No.: US 10,307,614 B2
(45) Date of Patent: Jun. 4, 2019

(54) SYSTEMS AND METHODS FOR SELECTING A RADIATION THERAPY TREATMENT PLAN

(71) Applicant: Accuray Incorporated, Sunnyvale, CA (US)

(72) Inventor: Eric Schnarr, Madison, WI (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 243 days.

(21) Appl. No.: 15/272,760

(22) Filed: Sep. 22, 2016

(65) Prior Publication Data

US 2018/0078784 A1 Mar. 22, 2018

(51) Int. Cl.
*A61N 5/10* (2006.01)

(52) U.S. Cl.
CPC .......... *A61N 5/1031* (2013.01); *A61N 5/1045* (2013.01)

(58) Field of Classification Search
CPC . A61N 5/00; A61N 5/10; A61N 5/103; A61N 5/1031; A61N 5/1001; A61N 5/1038; A61N 5/1039; A61N 5/1042; A61N 5/1045; A61N 5/1047; A61N 2005/1087; A61N 2005/1089; A61N 2005/109; A61G 13/00; A61G 13/02
USPC .......................................................... 378/65
See application file for complete search history.

(56) References Cited

U.S. PATENT DOCUMENTS

| 8,270,561 | B2 | 9/2012 | Zamyatin et al. |
| 8,401,148 | B2 | 3/2013 | Lu et al. |
| 8,986,186 | B2 | 3/2015 | Zhang et al. |
| 2010/0104068 | A1 | 4/2010 | Kilby et al. |

OTHER PUBLICATIONS

PCT/US2017/052758 International Search Report and Written Opinion of the International Searching Authority dated Nov. 27, 2017 (14 pages).

*Primary Examiner* — Jurie Yun
(74) *Attorney, Agent, or Firm* — Michael Best & Friedrich LLP (57) ABSTRACT

A method of selecting a radiation therapy treatment plan for a patient. The treatment plan is implemented through a radiation delivery system including a gantry capable of rotating around a couch, in which the couch is movable in a linear direction relative to the gantry. The movement of the couch and the gantry creates a helical delivery path having a pitch. A radiation module delivers a radiation beam, where the beam has a beam weight corresponding to a radiation fluence. The method includes receiving, by a controller, an objective including a desired dose, a desired dose distribution, or a dose constraint, optimizing the pitch to obtain an optimized pitch, optimizing, the beam weight to obtain optimized beam weight, determining, based on the optimized pitch and the optimized beam weight a treatment plan or a treatment dose, and outputting the treatment plan or the treatment dose.

28 Claims, 7 Drawing Sheets

SYSTEMS AND METHODS FOR SELECTING A RADIATION THERAPY TREATMENT PLAN

FIELD OF THE INVENTION

This invention generally relates to modulated radiation therapy for the treatment of cancer or the like, and specifically to a method for selecting a radiation therapy treatment plan for a patient.

SUMMARY OF THE INVENTION

Medical equipment for radiotherapy treats tumorous tissue with high energy radiation. A treatment plan is generated for the patient to accurately control the amount of radiation and its placement to ensure that the tumorous tissue receives sufficient radiation to be destroyed, and that the damage to the surrounding and adjacent non-tumorous tissue is minimized. Furthermore, the manner in which the radiation is delivered (e.g., angle, intensity, duration) can affect the quality and efficiency of the treatment plan.

The radiotherapy process typically involves treatment planning and treatment delivery. The radiotherapy process commonly begins with the acquisition of three-dimensional patient images, such as a computed tomography (CT) image or a magnetic resonance image (MRI). Next, relevant anatomical structures are delineated or contoured. These structures can be classified as either target areas to be irradiated, or sensitive structures to which radiation should be minimized. A treatment plan is then prepared that is optimized to maximize treatment to the target volumes while minimizing radiation to the sensitive structures.

Treatment planning attempts to avoid radiation to the healthy organs (e.g., spinal cord, heart, rectum, etc.) while delivering radiation to the tumor. More specifically, treatment planning aims to maximize the dose gradient between the target areas of radiation and organs at risk, which are healthy organs located near the tumor. Typically, a tumor of large volume will be treated from several different angles with the intensity and shape of a radiation beam adjusted appropriately. The purpose of using multiple beams, which converge on the site of the tumor, is to reduce the dose to areas of surrounding non-tumorous tissue. The angles at which the tumor is irradiated are selected to avoid angles which would result in irradiation of particularly sensitive structures near the tumor site. The angles and intensities of the beams for a particular tumor form the treatment plan for the tumor.

In radiotherapy applications, treatment planning also attempts to provide a uniform dose distribution within the tumor. Radiotherapy treatments deliver radiation in small increments—called fractions—to damage cancerous cells while allowing healthy cells a chance to recover. A uniform dose distribution in the tumor limits the damage to healthy cells in the tumor to recoverable levels, while still delivering enough radiation to damage cancerous cells and prevent them from growing.

Once a treatment plan is in place, the treatment plan is executed by and the prescribed radiation is delivered through a treatment delivery system. The treatment delivery system typically includes a couch that supports the patient and a gantry with a radiation source that rotates around the couch to deliver radiation to the tumor from different angles. As the gantry rotates, the couch translates in a linear direction relative to the gantry. Therefore, the radiation delivered from the radiation source on the gantry is delivered along a helical path. The helical delivery path is, in part, characterized by its pitch, which is a measure of the distance that the couch moves during one gantry rotation. Studies have shown that the pitch of the helical path created by the rotating gantry and the translating couch greatly affects the uniformity of the target dose distribution, and hence the quality and the efficiency of the treatment plan. However, there are some difficulties in choosing a pitch that is appropriate for the treatment. Accordingly, optimization of the pitch during the treatment planning phase can improve the overall treatment delivery.

As used herein, fluence is the number of photons or x-rays that crosses a unit of area perpendicular to a radiation beam. Fluence rate is the fluence per unit time. Intensity is the energy that crosses a unit area per unit time. Fluence and intensity are independent of what occurs in a patient, and more specifically are not dose. Dose is the amount of energy absorbed by tissue by virtue of radiation impacting the tissue. Radiation dose is measured in units of gray (Gy), where each Gy corresponds to a fixed amount of energy absorbed in a unit mass of tissue (e.g., 1 joule/kg). Dose is not the same as fluence, but increases/decreases as fluence increases/decreases.

The invention relates to a method of selecting a radiation therapy treatment plan for a patient. The treatment plan is implemented through a radiation delivery system including a gantry capable of rotating around a couch, in which the couch is movable in a linear direction relative to the gantry. The movement of the couch and the gantry creates a helical delivery path having a pitch. The radiation delivery system further includes a radiation module coupled to the gantry and capable of distributing a radiation beam, where the beam has a beam weight corresponding to a radiation fluence. The method includes receiving, by a controller, an objective including at least one from a list including a desired dose, a desired dose distribution, and a dose constraint, optimizing the pitch to obtain an optimized pitch, optimizing, the beam weight to obtain optimized beam weight, determining, based on the optimized pitch and the optimized beam weight at least one from the following list including a treatment plan and a dose, and outputting at least one of the treatment plan and the dose.

In another embodiment, the invention relates to a radiation therapy treatment system including a gantry having an aperture, and a couch configured to support a patient, where the couch is movable in a linear direction within the aperture. A radiation module is coupled to the gantry and rotatable around the couch the radiation module configured to deliver a radiation beam toward the patient. The radiation beam has a beam weight corresponding to a radiation fluence. The linear movement of the couch and the rotation of the radiation module create a helical path of radiation delivery, and the helical path has a pitch. A computer is in communication with the gantry, the radiation module, and the couch. The computer includes a controller configured to optimize the pitch of radiation delivery module, optimize the beam weight of the radiation beam, determine at least one of a treatment plan and a dose based on the optimized pitch and the optimized beam weight, and output the at least one of the treatment plan and the dose.

In yet another embodiment, the invention relates to a method of selecting a radiation therapy treatment plan for a patient. The treatment plan is implemented through a radiation delivery system including a gantry capable of rotating around a couch, where the couch is movable in a linear direction relative to the gantry, and a radiation module coupled to the gantry and capable of distributing a radiation beam, where the beam has a beam weight corresponding to a radiation fluence. The method includes receiving, by a controller, an objective including at least one from the list including a desired dose, a desired dose distribution, and a dose constraint, and receiving a first pitch and a first beam weight. The method further includes adjusting, by the controller, the first pitch using a first geometry to determine an adjusted pitch, adjusting, by the controller, the first beam weight using a second geometry to determine an adjusted beam weight, translating, by the controller, the adjusted beam weight from the second geometry to the first geometry; and calculating, by the controller, an adjusted dose based on the adjusted pitch and the adjusted beam weight, where the adjusted dose is represented in the first geometry.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. The use terms "optimize," "optimization," and "optimal" herein is meant to refer to an improvement or enhancement, and not limited to the ideal or best result.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium). As such, it should be noted that a plurality of hardware- and software-based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
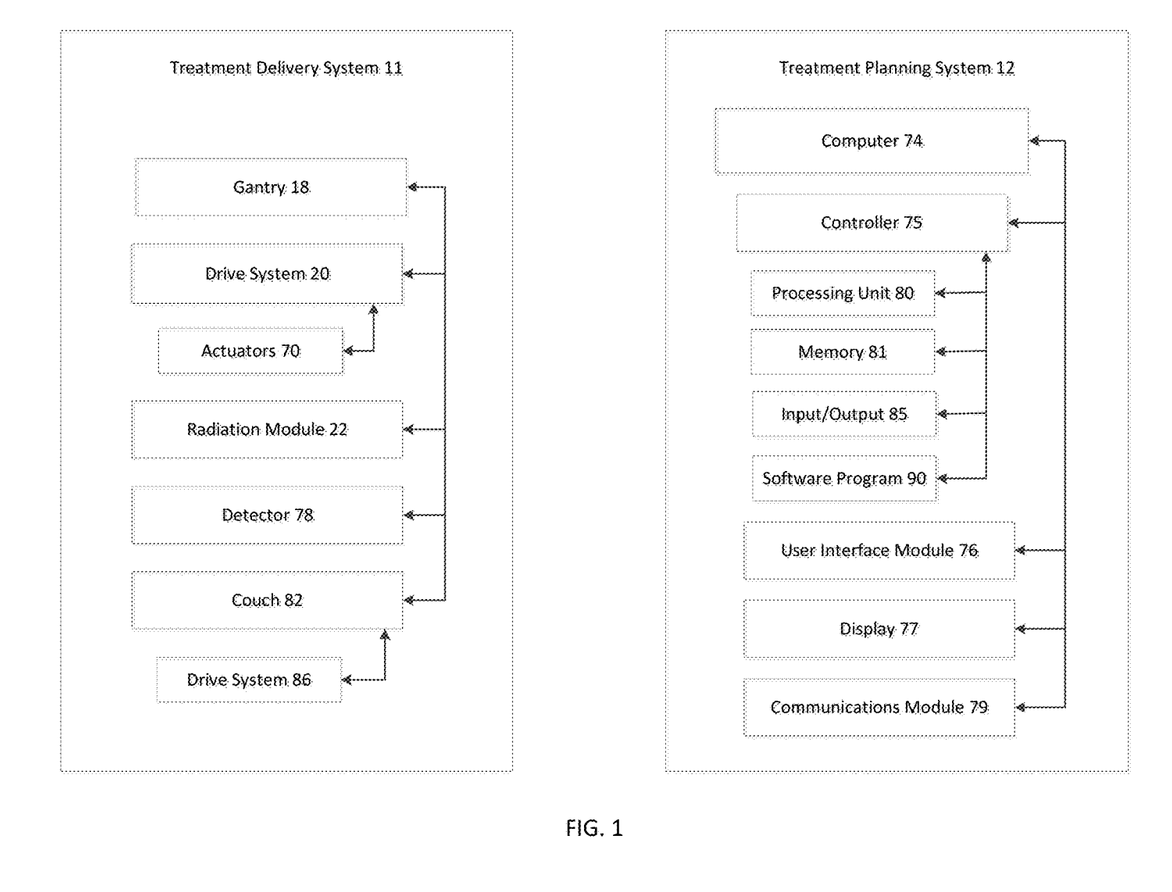
FIG. 1 is a schematic diagram of a radiation therapy treatment system.
Figure 2:
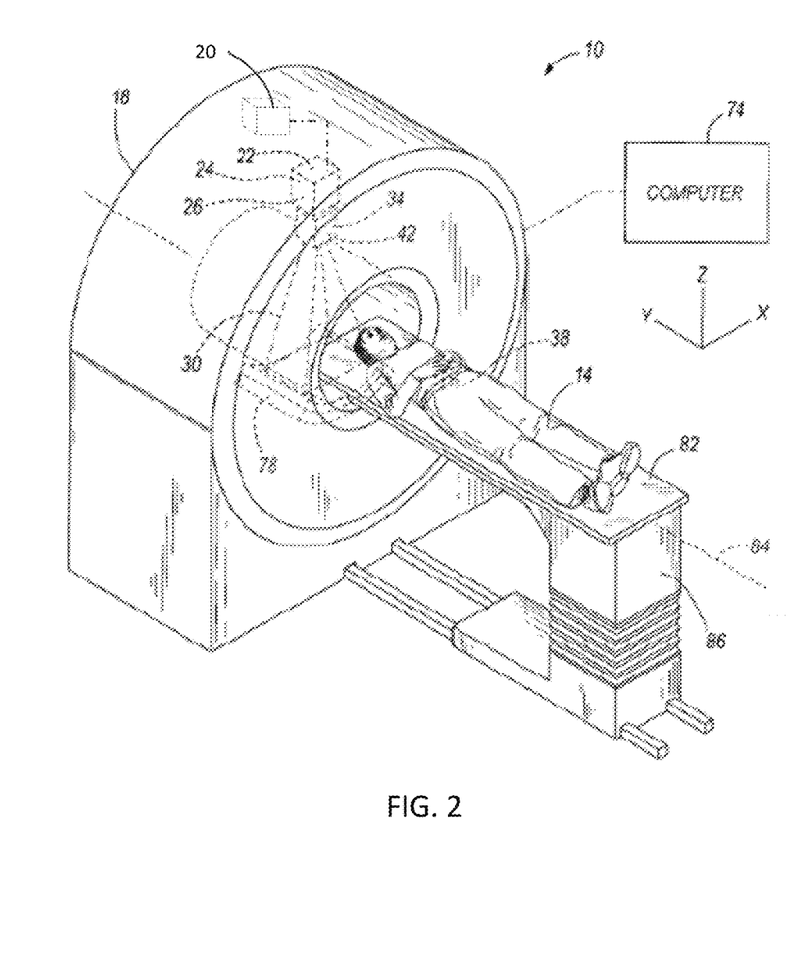
FIG. 2 is a perspective view of the radiation therapy treatment system.

FIGS. 1 and 2 illustrate a radiation therapy treatment system 10 that provides radiation therapy to a patient 14 according to one embodiment of the present invention. The radiation therapy treatment system 10 includes a treatment delivery system 11 and a treatment planning system 12. The radiation therapy treatment can include photon-based radiation therapy, brachytherapy, electron beam therapy, proton, neutron, particle therapy, or other types of treatment therapy.

Treatment Delivery System

The treatment delivery system 11 includes a gantry 18. The gantry 18 supports a radiation module 22, which includes a radiation source 24 and a linear accelerator (or LINAC) 26 that generates a beam 30 of radiation. Although the gantry 18 shown in FIG. 2 is a ring gantry (i.e., it extends through a full 360° arc to create a complete ring or circle), other types of mounting arrangements may also be employed. For example, a C-type, partial ring gantry, or robotic arm gantry arrangement could be used. Any other framework capable of positioning the radiation module 22 at various rotational and/or axial positions relative to the patient 14 may also be employed. In addition, the radiation source 24 may travel in a path that does not follow the shape of the gantry 18. For example, the radiation source 24 may travel in a non-circular path even though the illustrated gantry 18 is generally circular-shaped. The gantry 18 includes a drive system 20 that is operable to manipulate the position of the gantry 18 and/or the position of the radiation module 22 within the gantry 18. As used herein, the phrases "gantry rotation," "rotation of the gantry," and "movement of the gantry" are intended to refer to either movement of the gantry 18 or movement of the radiation module 22 within the gantry 18. The drive system 20 can be controlled by a computer 74 and/or controller 75 (herein after controller). The gantry 18 of the illustrated embodiment defines a gantry aperture 32 into which the patient 14 moves during treatment.

The radiation module 22 also includes a modulation device 34 operable to modify or modulate the radiation beam 30. The beam 30 generated by the radiation source 24 is shaped into a fan beam 30 by the modulation device 34. The fan shaped beam 30 can be conceptualized as many different beamlets 30A that, together, form the beam 30. In other embodiments, the beam 30 has a different shape. The modulation device 34 modulates the radiation beam 30 and directs the radiation beam 30 toward the patient 14. Specifically, the radiation beam 30 is directed toward a portion of the patient 14 containing a target 38. The patient 14 may also have more than one portion that needs to receive radiation therapy. The portion may include the patient's entire body, but is generally smaller than the patient's entire body and can be defined by a two-dimensional area and/or a three-dimensional volume. A portion may include one or more regions of interest. For example, a portion desired to receive the radiation, which may be referred to as a target 38 or target region, is an example of a region of interest. Another type of region of interest is a region at risk. If a portion includes a region at risk, the radiation beam 30 is preferably diverted from the region at risk. For example, the conceptualized beamlets 30A that are directed toward the region at risk can be blocked or limited by the modulation device 34, while the conceptualized beamlets 30A that are directed toward the target 38 can pass through the modulation device 34.

Such modulation is sometimes referred to as intensity modulated radiation therapy ("IMRT"). IMRT is a generic term for a number of radiotherapy techniques that, essentially, vary the beam intensity that is directed at the patient. The modulation device 34 can vary the beam 30 spatially, temporally, or both. The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

Figure 3:
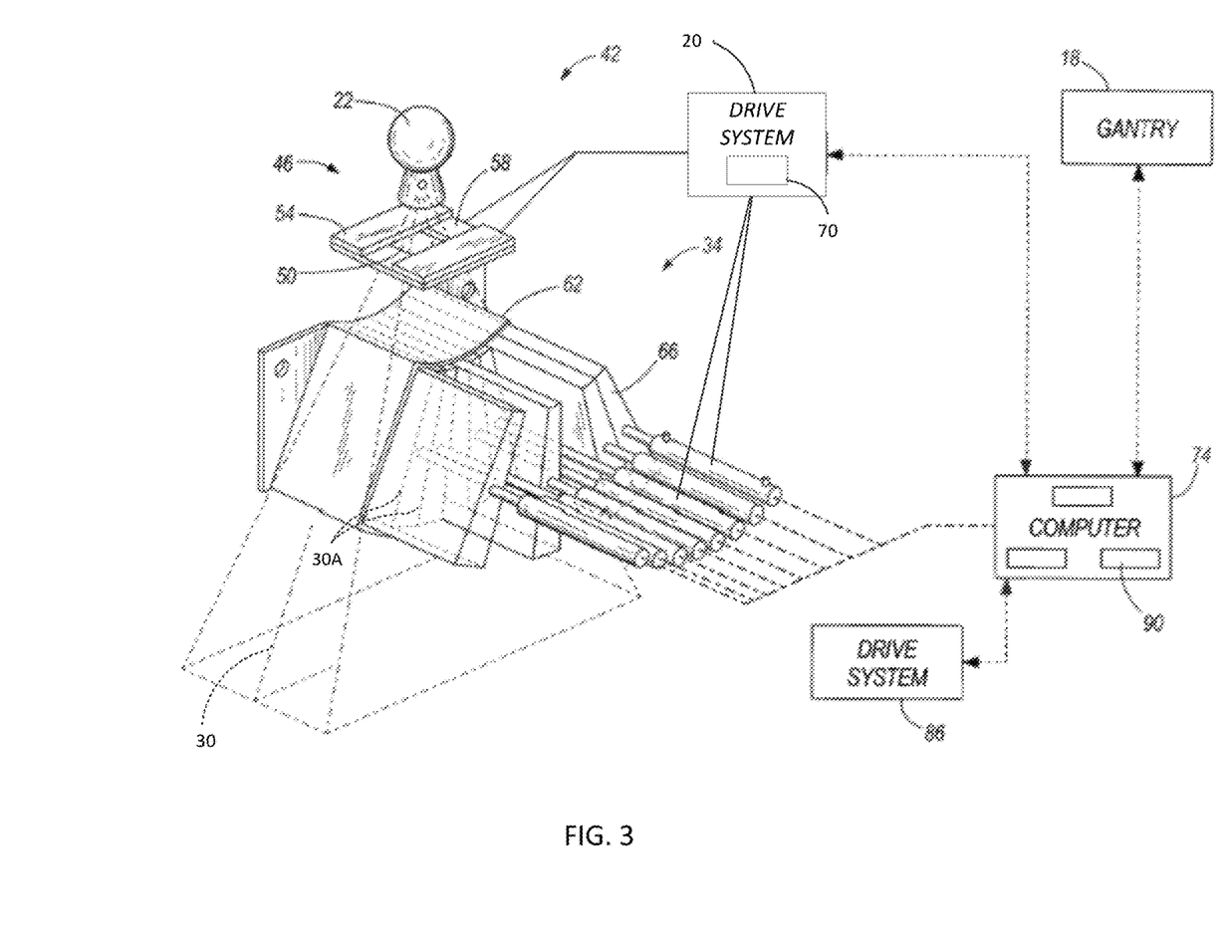
FIG. 3 is a perspective view of a multi-leaf collimator that can be used in the radiation therapy treatment system illustrated in FIG. 2.

In one embodiment, and illustrated in FIG. 3, the modulation device 34 can comprise a multi-leaf collimator 62 (or MLC), which includes a plurality of interlaced leaves 66 operable to move from a first position to a second position, to provide intensity modulation of the radiation beam 30. It is also noted that the leaves 66 can move to a position anywhere between a minimally-open position and maximally-open position. The plurality of interlaced leaves 66 modulate the strength, size, and shape of the radiation beam 30 before the radiation beam 30 reaches the target 38 on the patient 14. Modulation of the beam 30 occurs by sequentially and monotonically moving the leaves 66 into desired positions to block or expose specific beamlets 30A, thus achieving the desired shapes of the beam 30 as a whole. The amount of time a conceptualized beamlet 30A is exposed is one way to control the amount of radiation delivered by that beamlet 30A. Each of the leaves 66 is independently controlled by an actuator 70, such as a motor or an air valve so that the leaf 66 can open and close quickly to permit or block the passage of radiation. The actuators 70 can be controlled by the computer 74 and/or controller 75. In the illustrated embodiment, the actuators 70 are a component of the drive system 20 that controls the gantry 18.

Conceptually, the leaves 66 can be controlled to each selectively allow or block a beamlet 30A from passing through the modulation device 34 and on to the target 38. By independently controlling the leaves 66, the modulation device 34 can block certain beamlets 30A and allow other beamlets 30A. In some embodiments, the leaves 66 operate in a binary manner, whereby the leaves 66 move directly from a fully opened position to a fully closed position. When the leaves 66 operate in a binary manner, the modulation device 34 is often configured to modulate the intensity of the beam 30 temporally. Temporally modulating the beam 30 involves controlling the amount of time each leaf 66 remains open or closed, and thus, the about of time each beamlet 30A is exposed. The more radiation desired from a beamlet 30A, the longer the leaf 66 remains open. The amount of time a leaf 66 stays open is referred to as a leaf-open time. In other embodiments, the modulation device 34 can modulate the intensity of the beam 30 spatially. Specifically, the leaves 66 can move to various positions between the fully opened position and fully closed position to partially block or reduce the portion of the beamlet 30A passing through. In some embodiments, the modulation device 34 uses a combination of temporal and spatial modulation techniques.

Regardless of whether the beamlets 30A are modulated temporally or spatially, each beam is modulated to have a beamlet weight. A beamlet weight corresponds to the fluence of the radiation and the dose received by the target 38. A sinogram contains information regarding the modulation of the beam 30. When the beamlets 30A are temporally modulated, the sinogram contains information about the amount of time each leaf 66 is open relative to the total projection time. The sinogram is then used to guide the delivery of the radiation. As will be explained in further detail below, the beamlet weights and the corresponding sinogram are calculated and optimized by the treatment planning system 12.

With further reference to FIG. 1, the treatment delivery system 11 can also include a detector 78, e.g., a kilovoltage or a megavoltage detector that receives the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the controller 75 for processing of the absorption data and generating images of the patient's body tissues and organs. The images can also illustrate bone, soft tissues, and blood vessels.

The CT images can be acquired with a radiation beam 30 that has a fan-shaped geometry, a multi-slice geometry, or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified targets 38 made through a contouring process. The newly acquired CT images for the patient 14 can be registered with the previously acquired CT images to assist in identifying the targets 38 in the new CT images. The registration process can use rigid or deformable registration tools. The image data can be presented on a display as either a three-dimensional image or a series of two-dimensional images. In addition, the image data comprising the images can be either voxels (for three-dimensional images) or pixels (for two-dimensional images). The term image element is used generally in the description to refer to both.

The treatment delivery system 11 also includes a patient support device, such as a couch 82 (illustrated in FIG. 2), which supports the patient 14. The couch 82, or at least portions thereof, moves into and out of the field of radiation along an axis 84. The couch 82 is also capable of moving along the X and Z axes as illustrated in FIG. 2. In other embodiments of the invention, the patient support can be a device that is adapted to support any portion of the patient's body. The patient support is not limited to having to support the entire patient's body. The system 11 also can include a drive system 86 operable to manipulate the position of the couch 82. The drive system 86 can be controlled by the controller 75. The couch 82 can be controlled to move at a constant speed through the gantry or can be controlled to start and stop at certain intervals. The couch 82 also can be controlled to move at a varying speed through the gantry. The treatment plan can include instructions that are delivered to the controller 75 to move the couch 82 at a constant speed or varying speed through the gantry or to start and stop the couch 82 at certain intervals. The treatment plan may also be adjusted "on the fly" to adjust the planned movement of the couch as a treatment is being delivered to accommodate unexpected changes in anatomy or patient movement during the treatment. These "on the fly" changes may be incorporated into the treatment plan or the treatment delivery system may just make the changes for the particular treatment fraction.

During treatment delivery, the controller 75 controls the drive systems 20 and 86 to manipulate the positions of the gantry 18 and the couch 82, respectively, to enable the radiation module 22 to direct radiation toward the target 38 from different angles and sides. In the illustrated embodiment, the controller 75 controls the drive system 86 to move the couch 82 along the axis 84, into and out of the aperture 32 of the gantry 18. Thus, the couch 82 translates relative to the gantry 18. At the same time, the controller 75 controls the drive system 20 to rotate the gantry 18 and/or radiation module 22 around the couch 82. Together, the rotational movement of the gantry 18 and the linear translation of the couch 82 create a helical path of radiation delivery.

The helical trajectory of the radiation is characterized, in part, by its pitch. The pitch of a helix is defined as the height of one complete helix turn, measured parallel to the axis of the helix. In the illustrated embodiment, the helical trajectory is accomplished by the combined movement of the gantry and the couch. Accordingly, with respect to the treatment delivery system 11 described herein, pitch is a measure of the linear movement of the couch 82 relative to the rotational movement of the gantry 18. In other words, a specific pitch of the helix can be achieved by controlling the movement of the gantry 18 and the couch 82 relative to one another.

One complication with helical radiation delivery is the helical junctioning effect, or the "thread effect." When delivering radiation in a helical path, the distance between the radiation source 24 and the target 38 (i.e., the source-to-point distance) varies as the gantry 18 rotates to different angles around the axis 84. This is true for any target 38 that is off axis, meaning not located along the axis 84 of rotation of the gantry 18. In the illustrated embodiment, any target 38 that is not positioned along the y-axis 84 will have a varying source-to-point distance as the gantry 18 rotates about the y-axis. Because the source-to-point distance varies, the fluence of radiation also varies with the rotation of the gantry 18, causing a ripple (i.e., non-uniformity) in the dose delivered. This ripple in dose delivery is commonly referred to as the thread effect. It has been determined that the particular helical path, and specifically the pitch of the helix, used to deliver radiation can affect the degree of the thread effect. Accordingly, one aspect of the treatment planning system aims to optimize the pitch of the helical path used to deliver radiation therapy.

Treatment Planning System

The treatment planning system 12 is used to personalize the radiation therapy to the person 14 being treated. The treatment planning system 12 helps identify characteristics of the target 38 (e.g., size, location, etc.) and any at-risk areas. The treatment planning system 12 then helps create a treatment plan that is adapted to these characteristics. The treatment plan may include a prescribed dosage and a dose distribution such as a dose volume histogram (DVH). The treatment plan may also identify the parameters for administering the prescribed dosage. For example, in some embodiments, the treatment plan includes a breakdown of the number of radiation therapy sessions needed (i.e., fractions), and a specific treatment plan and dosage for each session. In addition, the treatment plan may specify the parameters of the treatment delivery system 11 for administering the radiation therapy. For example, the treatment plan may include instructions for the machine that specify the speed of the couch 82 and the gantry 18, the pitch, and the leaf modulation parameters, such as leaf open times and/or beamlet weights.

Pitch is one of the parameters that can be selected during the treatment planning phase in order to reduce the thread effect and optimize the treatment plan. As previously mentioned, the particular helical path, and specifically the pitch, used to deliver radiation can affect the quality and efficiency of the treatment plan. In the illustrated embodiment, the pitch is a measure of the linear movement of the couch 82 relative to the rotational movement of the gantry 18. More specifically, the pitch can be defined as the fraction of a field width that the couch 82 moves during one rotation of the gantry 18. In other embodiments, the definition of pitch can vary depending upon the manner in which the helical path of delivery is achieved. For example, in other embodiments, helical radiation delivery may be created by rotating and translating the gantry while holding the couch at a fixed position.

Choosing an optimal pitch of the helix can decrease the thread effect, resulting in a more uniform distribution of the radiation. Studies have identified at least four factors that impact the thread effect, including beam divergence, the inverse square law, attenuation, and the cone effect. These factors result in different optimal pitch values for each patient. In a given treatment plan, there may be more than one optimal pitch value that reduces the thread effect and helps to produce a more uniform distribution of radiation.

Choosing an optimal pitch can be difficult due to the number of factors that are considered when choosing a pitch. Furthermore, a pitch that is slightly different from one of the optimal pitches can result in a sharp degradation in dose uniformity and/or delivery efficiency. Another difficulty in selecting an optimal pitch arises when modulating beamlet 30A and selecting optimal beamlet weights. In many current systems, the pitch and the beamlet weights cannot be optimized unilaterally. Rather, once a pitch is selected, the beamlets 30A are modulated based on the selected pitch. If it is later determined that a different pitch should be used, modulation of the beam 30 is often restarted from the beginning of the process. The treatment planning system 12 described herein provides a system and method for selecting a radiation therapy treatment plan that allows for simultaneous optimization of the pitch and modulation of the beam 30.

The treatment planning system 12 includes the computer 74, which is embodied as an operator station to be accessed by medical personnel. The computer 74 includes a controller 75, a user interface module 76, a display 77, and a communications module 79. The controller 75 and the user interface module 76 include combinations of software and hardware that are operable to, among other things, control the operation of the treatment delivery system 11 and the information that is presented on the display 77.

The controller 75 includes, for example, a processing unit 80 (e.g., a microprocessor, a microcontroller, or other suitable programmable device), a memory 81, and software program 90. The processing unit 80 may represent one or more general-purpose processors, a special purpose processor such as a digital signal processor or other type of device such as a controller or field programmable gate array.

It should be understood that although the controller 75, the user interface module 76, the display 77, and the communications module 79 are illustrated as part of a single server or computing device, the components of the treatment planning system 12 can be distributed over multiple servers or computing devices. Similarly, the treatment planning system 12 can include multiple controllers 75, user interface modules 76, displays 77, and communications modules 79.

The memory 81 includes, for example, a read-only memory ("ROM"), a random access memory ("RAM"), an electrically erasable programmable read-only memory ("EEPROM"), a flash memory, a hard disk, an SD card, or another suitable magnetic, optical, physical, or electronic memory device. The processing unit 80 is connected to the memory 81 and executes the software program 90 that is capable of being stored in the RAM (e.g., during execution), the ROM (e.g., on a generally permanent basis), or another non-transitory computer readable medium such as another memory or a disc. Additionally or alternatively, the memory 81 is included in the processing unit 80. The controller 75 also includes an input/output ("I/O") system 85 that includes routines for transferring information between components within the controller 75 and other components of the treatment planning system 12. Software included in the implementation of the treatment planning system 12 is stored in the memory 81 of the controller 75. The software includes, for example, firmware, one or more applications, program data, one or more program modules, and other executable instructions. The controller 75 is configured to retrieve from memory and execute, among other things, instructions related to the methods described below.

The user interface module 76 is configured for user control of the treatment planning system 12 and to input various parameters into the treatment planning system 12. For example, the user interface module 76 is operably coupled to the controller 75 to control the information presented on the display 77. In one embodiment, a user uses the interface module 76 to enter a plurality of machine parameters and clinical data that is used to optimize and create treatment plan(s). The user interface module 76 can send information inputted by user to the controller 75 and/or processing unit 80. The user interface module 76 can include a combination of digital and analog input or output devices required to achieve a desired level of control for the treatment planning system 12. For example, the user interface module 76 can include input devices such as a touch-screen display, a plurality of knobs, a plurality of dials, a plurality of switches, a plurality of buttons, or the like.

The display 77 is, for example, a liquid crystal display ("LCD"), a light-emitting diode ("LED") display, an organic LED ("OLED") display, an electroluminescent display ("ELD"), a surface-conduction electron-emitter display ("SED"), a field emission display ("FED"), a thin-film transistor ("TFT") LCD, or the like. In other constructions, the display 77 is a Super active-matrix OLED ("AMOLED") display.

In some implementations, the treatment planning system 12 is also configured to connect to a network 94 (e.g., a WAN, a LAN, or the like) via the communications module 79 to access other programs, software, or treatment planning systems 12, or treatment delivery systems 11. The communications module 79 can include a network interface, such as an Ethernet card or a wireless network card that allows the treatment planning system 12 to send and receive information over a network, such as a local area network or the Internet. In some embodiments, the communications module 79 includes drivers configured to receive and send data to and from various inputs and/or output devices, such as a keyboard, a mouse, a printer, etc. Data communications can occur via a wireless local area network ("LAN") using any of a variety of communications protocols, such as Wi-Fi, Bluetooth, ZigBee, or the like. Additionally or alternatively, data communications can occur over a wide area network ("WAN") (e.g., a TCP/IP based network or the like).

The communications module 79 is also compatible with the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIGS. 1 and 3 generally represent two-way communication and information transfer where indicated. However, for some medical and computerized equipment, only one-way communication and information transfer may be necessary.

The processing unit 80 executes instructions stored in the computer-readable media. The instructions can include various components or modules configured to perform particular functionality when executed by the processing unit 80. For example, the software program 90 includes a plurality of modules or applications that interact or communicate with one another to provide instructions to the processing unit 80 for generating a treatment plan for a patient, modifying or adapting a treatment plan, acquiring images of the patient, and controlling the components of the treatment delivery system 11. It is to be understood that the software program 90 can include variety of modules in addition to the modules that are described in detail below.

Figure 4:
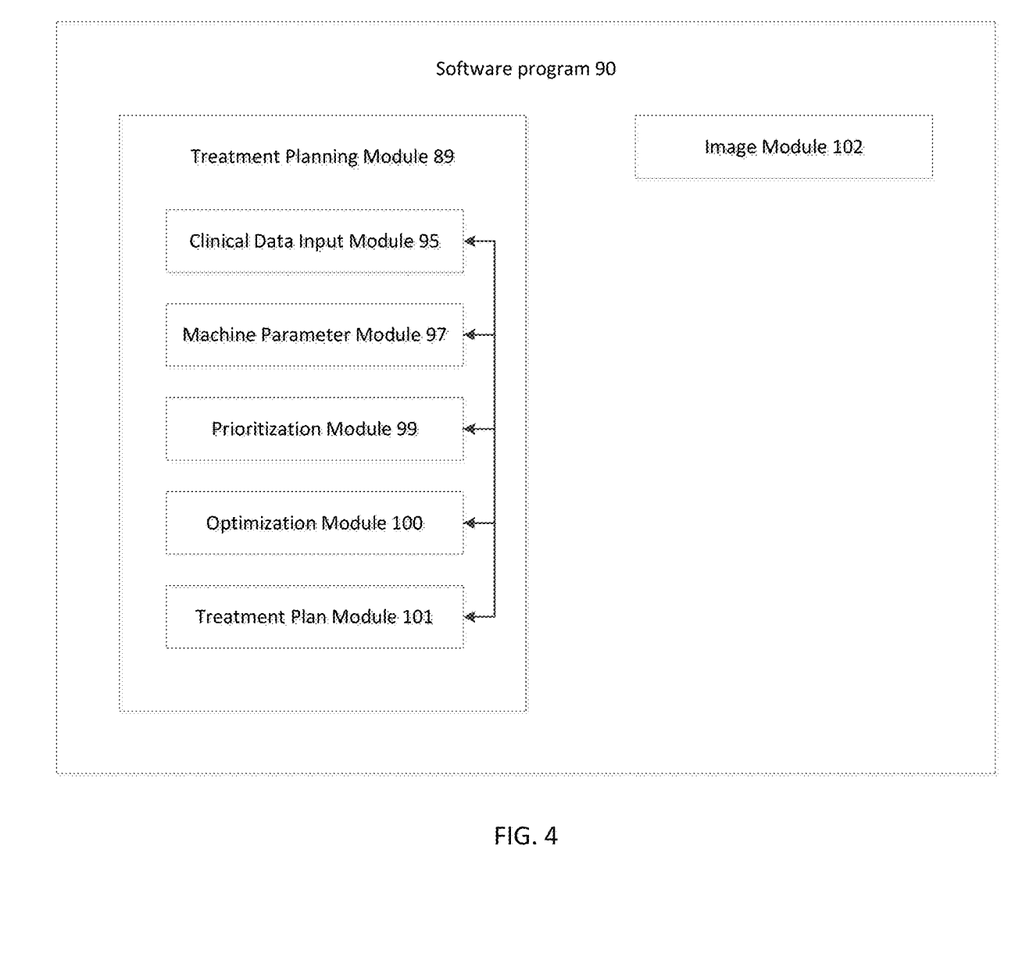
FIG. 4 a schematic diagram of a software program used in the radiation therapy treatment system.

The software program 90 includes a treatment planning module 89 that interacts with the user interface module 76 and the other components of the controller 75 to create a patient's treatment plan and to display on the display 77 various "screens" or "pages" related to the treatment plan. The screens of the user interface may include, but are not limited to images, charts, diagrams, fields, columns, rows, dialog boxes, tabs, buttons, radio buttons, and drop down menus. The screens of the user interface are not limited to any particular arrangement.

In one embodiment, the treatment planning system 12 can represent a server that hosts the treatment planning module 89 as a network-based tool or application. Therefore, a user can access the treatment planning module 89 through a network, such as the Internet. Accordingly, in some embodiments, a user is not required to have the treatment planning module 89 permanently installed on the controller 75. Rather, the user can access the treatment planning module 89 using a browser application, such as Internet Explorer® or Google Chrome.

The treatment planning module 89 can include a plurality of submodules. FIG. 4 illustrates the software program 90 and the treatment planning module 89 in a greater detail. In one embodiment, the treatment planning module 89 includes a clinical data input module 95, a machine parameter module 97, a prioritization module 99, an optimization module 100, and a treatment plan generation module 101. The functionality of these submodules is explained in more detail below. In other embodiments, the treatment planning module 89 can include more or fewer modules that provide different functionality to the treatment planning system 12.

As shown in FIG. 4, the software program 90 also includes an image module 102 operable to acquire or receive images of at least a portion of the patient 14. The image module 102 can generate instructions for the on-board or on-line image device, such as a CT imaging device to acquire images of the patient 14 before treatment commences, during treatment, and after treatment according to desired protocols. For example, the on-board or on-line image device can comprise the radiation source and the detector, where the radiation source delivers kV or MV radiation to the patient that is collected by the detector and processed into a three-dimensional (e.g., CT) image. For CT images, the data comprising the patient images are composed of image elements, which represent image elements stored as data in the radiation therapy treatment system. These image elements may be any data construct used to represent image data, including two-dimensional pixels or three-dimensional voxels. The images can be stored in memory or in a database and retrieved by the image module 102 for later use. The images can be used by the treatment planning module 89 to create a treatment plan for the patient 14.

In one aspect, the image module 102 acquires an image of the patient 14 while the patient 14 is substantially in a treatment position. Other off-line imaging devices or systems may be used to acquire pre-treatment images (e.g., three-dimensional) of the patient 14, such as non-quantitative CT, MRI, PET, SPECT, ultrasound, transmission imaging, fluoroscopy, RF-based localization, and the like. The acquired images can be used for determining the relative location of the target region and the sensitive structures. Further, the acquired images can be used for registration/alignment of the patient 14 with respect to the gantry or other point and/or to determine or predict a radiation dose to be delivered to the patient 14. The acquired images also can be used to determine a radiation dose that the patient 14 received during the prior treatments. The image module 102 also is operable to acquire images of at least a portion of the patient 14 while the patient is receiving treatment to determine a radiation dose that the patient 14 is receiving in real-time.

The clinical data input module 95 allows a user to input different clinical goals and constraints (together "objectives") related to the treatment of the patient 14. The objectives can include the prescribed, or desired dose. The specific clinical objectives generally depend on the patient's morphology or condition to be treated. Specifically, the clinical objectives depend on the region of interest (e.g., the type and/or size of tumor) of the patient 14 that will be treated by the system 10. Further, the clinical objectives depend on specific radiation dose treatment values for each region of interest. In one embodiment, the clinical objectives can include: aggressive treatment, sensitive structure sparing, etc. If the focus of the treatment process is a lung tumor, the clinical data inputted through the data input module 95 will depend on the tumor location and the radiation dose generally associated with treating a lung tumor. In one embodiment, the clinical data is directly inputted to the clinical data input module 95 by a user (e.g., via the user interface module 76). In other embodiments, the clinical data input module 95 automatically retrieves the clinical data that is stored in the memory 81. The clinical data input module 95 allows a user to input or select a plurality of clinical objectives at the same time.

The machine parameter module 97, allows a user to input or select a plurality of machine parameters to be used in the treatment planning module 89. These machine parameters are user-visible parameters that are used to control specific aspects of the radiation delivery to the patient. For example, the machine parameters are related to the gantry, the radiation delivery device, and the couch. In one embodiment, the machine parameters can include: a jaw width, a pitch, a gantry speed, a couch speed, a gantry position, and a couch position. Further, the machine parameters can include the type of radiation delivery: a helical radiation treatment delivery, a static radiation treatment delivery, a rocking gantry radiation treatment delivery, and a running start/stop radiation treatment delivery. In one embodiment, the machine parameters are directly inputted to the machine parameter module 97 by a user (e.g., via the user interface module 76). In other embodiments, the machine parameter module 97 automatically retrieves machine parameters that are stored in the memory 81. After the machine parameters are inputted into the machine parameter module 97, a user can select one or more machine parameter to be used in creating a treatment plan.

The prioritization module 99 prioritizes at least one of the clinical objectives selected by the clinical data input module 95. Some of the clinical objectives have limits or fixed values and other clinical objectives are flexible and can be adjusted during the process of optimizing and generating a treatment plan, which will be explained in greater detail below. For example, the radiation dose delivered for treatment of the spinal cord can not exceed a specific value because a very high radiation dose will damage the spinal cord. In some embodiments, the prioritization module 99 operates concurrently with the optimization module 100. For example, the optimization module 100 optimizes the flexible parameters while abiding by the fixed limitations set by the prioritization module.

The optimization module 100 optimizes a prioritized clinical objective with a selected machine parameter. In some embodiments, when a user selects more than one machine parameter, the optimization module 100 optimizes the prioritized clinical objective with all of the selected machine parameters. The optimization module 100 converts user inputs into detailed machine instructions that are forwarded to the radiation treatment device in the form of a treatment plan. The radiation treatment device receives these machine instructions and produces the planned radiation treatment dose. As mentioned above, the optimization module 100 operates concurrently with the prioritization module 99. The optimization processes is a continuous process. The optimization module 100 optimizes the prioritized clinical objective with the selected machine parameter, the user views the result, and then the user can optimize a different clinical objective with the machine parameter. Therefore, the optimization module 100 can simultaneously optimize multiple set of machine instructions. Additionally, in some embodiments, the optimization module 100 can execute an optimization process during the delivery of the treatment.

The treatment plan generation module 101 includes instructions for generating a treatment plan for the patient 14 based on the data generated from at least one of the other modules, including the data input module 95, the machine parameter module 97, the optimization module 100, and the prioritization module 99. The treatment plan generation module 101 can generate several treatment plans with the data received from the sub modules 95, 97, 99, and 100. Further, the treatment plan generation module 101 can use data inputted to the system 10 by medical personnel, retrieved from memory or a database, received from other modules, or otherwise acquired by the system 10. The data can include one or more images (e.g., planning images and/or pre-treatment images) of at least a portion of the patient 14. These images may be acquired and processed by an image module 102 in the manner described in the preceding paragraphs. The generated treatment plans provide instructions for the delivery of treatment radiation to the patient 14. For example, the treatment plans include a radiation dose distribution for the target region. The treatment plan generation module 101 can separate a treatment plan into a plurality of treatment fractions and can determine the radiation dose for each fraction or treatment based on a radiation dose prescription input by medical personnel. The process of separating the treatment plan into fractions is referred to as fractionation.

After the treatment plans are generated, a user can select one of the generated plans to be used for the patient 14. The treatment delivery system 11 delivers radiation to the patient 14 according to the selected treatment plan. For example, the patient 14 receives the radiation dose prescribed for each fraction of the treatment plan. Prior to delivery of each fraction, the patient is positioned on the couch 82 and registered or aligned with respect to the treatment delivery system 11. It is to be understood that the treatment plan is not static and can change throughout the course of treatment. For example, the treatment plan can be adapted to incorporate changes (e.g., anatomical changes, machine parameter changes, etc.) discovered while delivering one of the fractions. The treatment plan then implements those changes in future fractions.

FIGS. 5-8 illustrate various methods for selecting a radiation therapy treatment plan. The various methods described herein can be executed by the processing unit 80 of the controller 75 with the assistance of the software program 90 and the treatment planning modules 89 and sub-modules 95, 97, 99, 100, 101. Various steps described herein with respect to the methods are capable of being executed simultaneously, in parallel, or in an order that differs from the illustrated serial manner of execution. The methods are also capable of being executed using additional or fewer steps than are shown in the illustrated embodiment.

Figure 5:
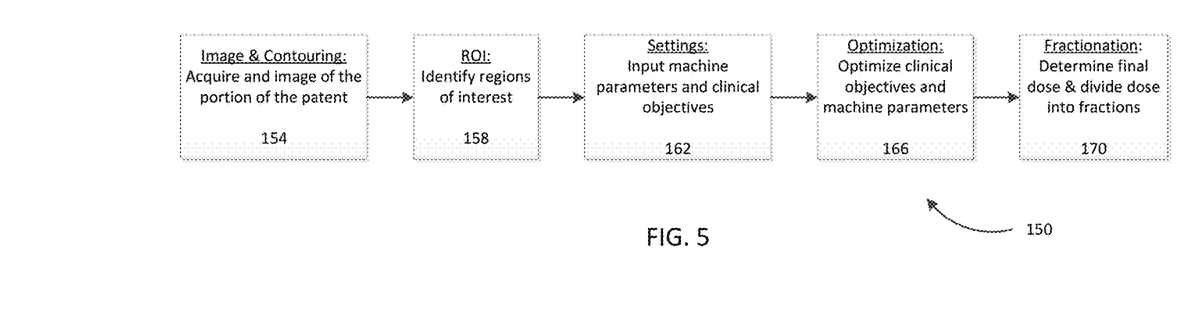
FIG. 5 is a flow chart of a method for selecting a radiation therapy treatment plan for a patient according to an embodiment of the invention.

FIG. 5 is a flow chart illustrating a method 150 of selecting a radiation therapy treatment plan according to an embodiment of the invention. The method 150 includes acquiring an image of the portion of the patient 14 containing the target 38 (step 154) and contouring the image if desired. The image can be acquired using the image module 102 in conjunction with the treatment delivery system 11, as describe above. The image is used to identify the regions of interest (ROI) (step 158). For example, the target 38 is identified as well as regions of risk and sensitive structures.

Information obtained during steps 154 and 158 can be inputted into the clinical data input module 95. In addition, clinical objectives (i.e., goals and constraints) can be added to the clinical data input module 95 and the prioritization module 99 (step 162). The user also inputs a series of plan settings into the machine parameter module 97 (step 162). For example, the settings can include, among other settings, the type of delivery mode, the field width, the jaw mode, and pitch. The data inputted throughout the method 150 can be entered through user interface module 76 and stored on the memory 81. If desired, the user can utilize the prioritization module 99 to prioritize objectives.

The treatment planning system 12 then engages in an optimization process (step 166) to calculate an optimal treatment plan that reconciles the machine parameters against the clinical objectives. Specifically, the controller 75 communicates with the optimization module 100 and executes instructions to determine optimal machine parameters for delivering treatment based on the data entered into the clinical data module 95, the machine parameter module 97, and the prioritization module 99.

Once the optimization module 100 completes the optimization process and calculates a treatment plan, the controller 75 executes a fractionation process with the assistance of the treatment plan module 101 (step 170). During the fractionation process treatment plan module 101 uses the treatment plan calculated during the optimization process (step 166) determines the radiation dose for each fraction of the treatment. In other words, the total treatment plan is split up into different doses that will be administered during a number of different treatment sessions, each of which delivers a fraction of the total prescribed dose.

Figure 6:
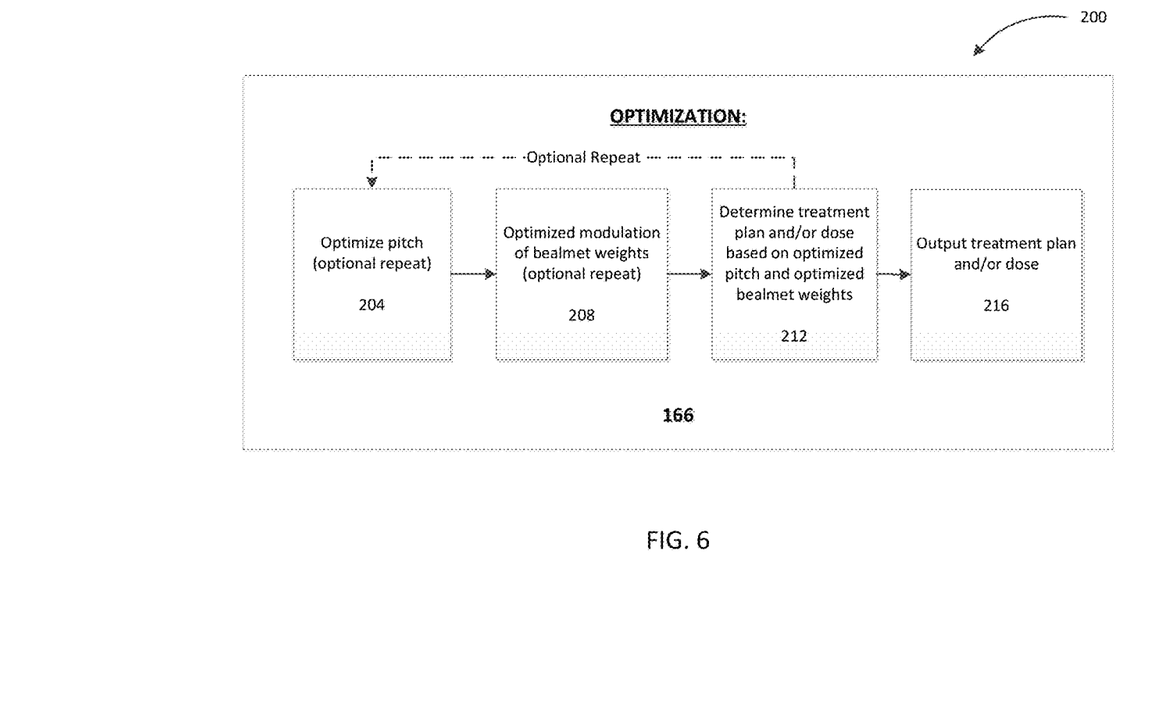
FIG. 6 is a flow chart of a method of optimizing the treatment therapy system according to an embodiment of the invention.
Figure 7:
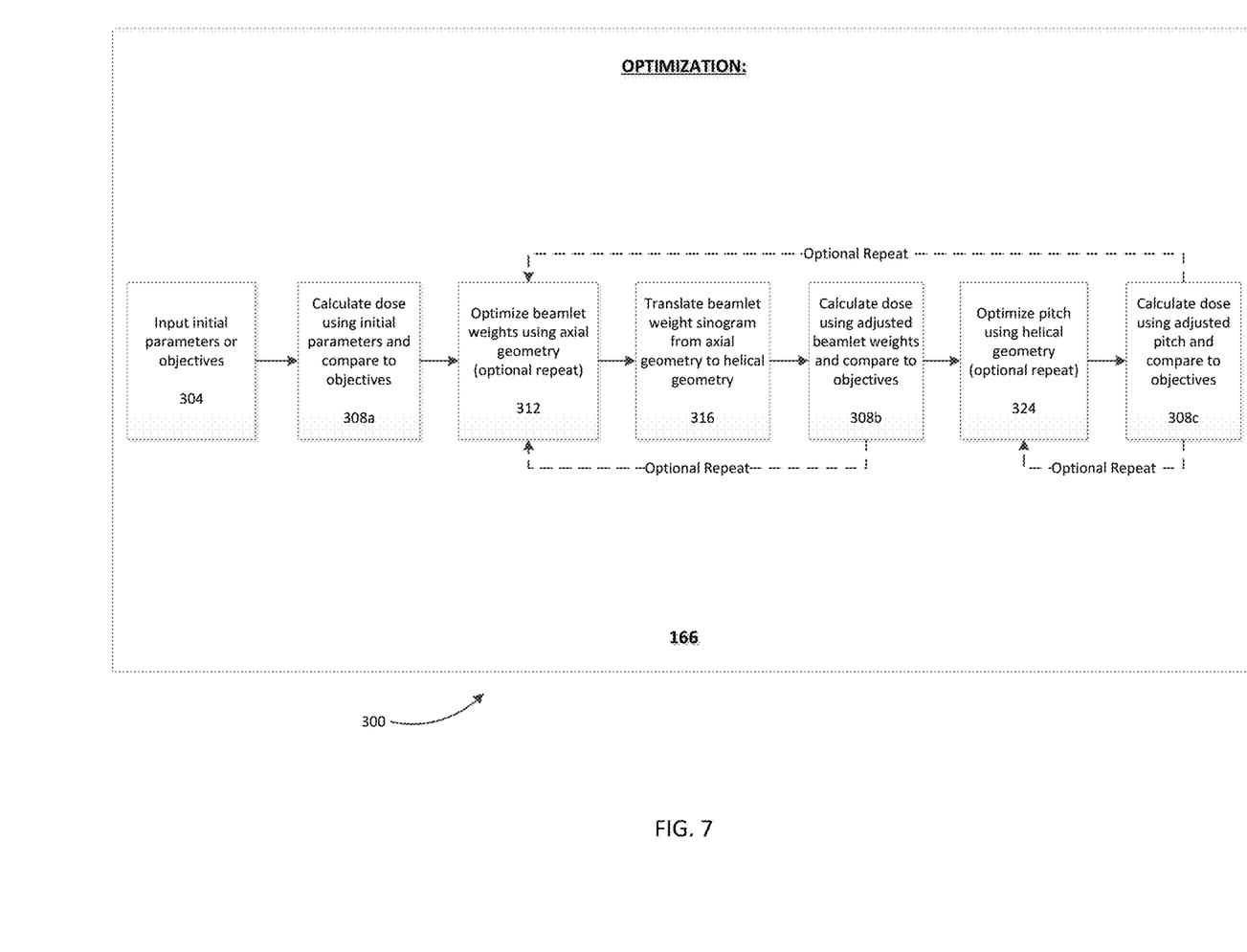
FIG. 7 is a flow chart of a method of optimizing the treatment therapy system according to an embodiment of the invention.
Figure 8:
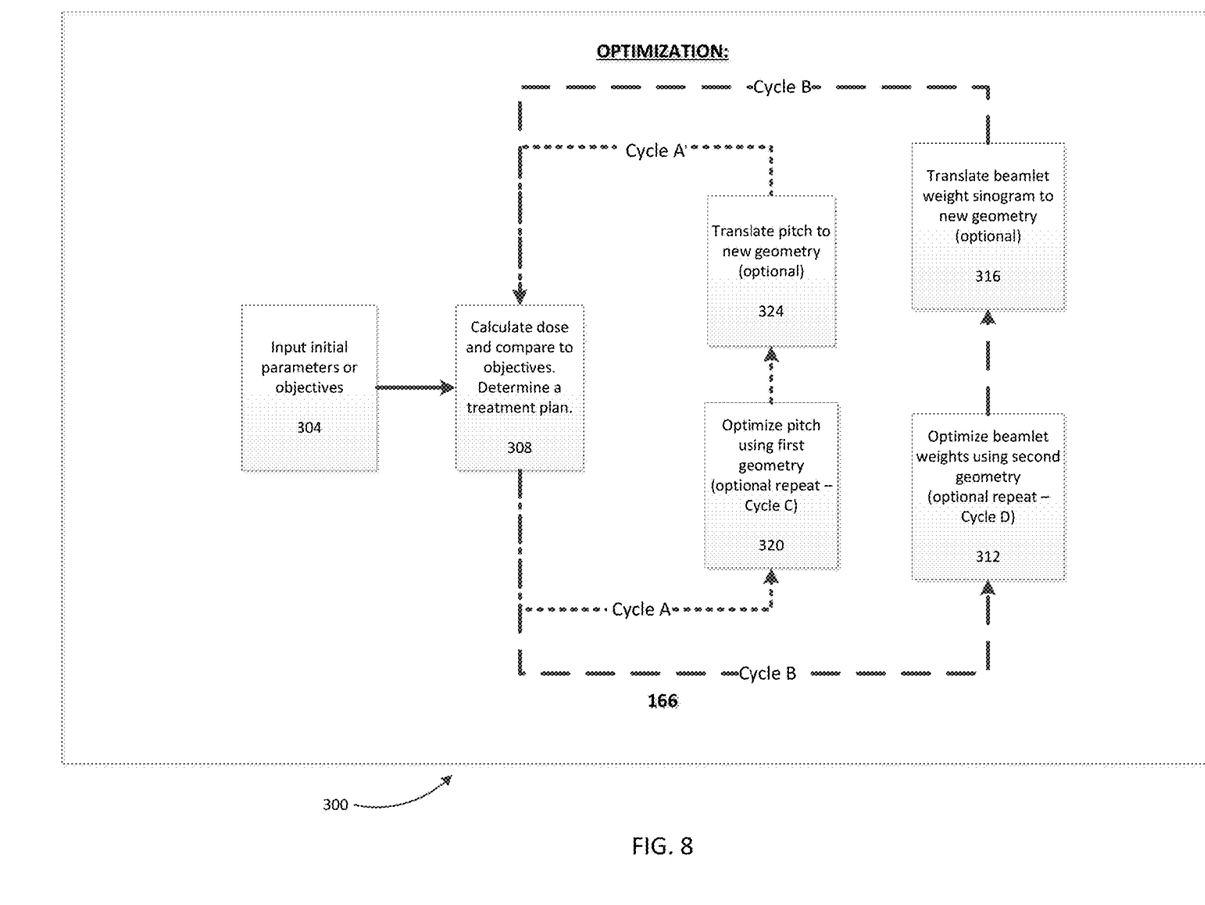
FIG. 8 is a flow chart illustrating various cycles of optimizing the treatment therapy system according to an embodiment of the invention.

FIGS. 6-8 illustrate various methods 200 and 300 of carrying out the optimization process of (step 166) of method 150 according to one embodiment. These methods 200 and 300 seek to optimize the parameters of the treatment delivery system 11 to achieve the prescribed dose. Many aspects of the different methods 200 and 300 are interchangeable and can be recombined into other methods. The pitch of the treatment delivery system 11 and the beamlet weights are two of the parameters that can be optimized by the methods 200 and 300. More specifically, a pattern of leaf open times and beamlet weights is determined for each beamlet 30A in order to achieve the objective or the prescribed dose. This information relating to the modulation of the beamlets 30A can be represented by a sinogram, which is used to guide the delivery of radiation.

The methods 200 and 300 are capable of optimizing the pitch to reduce the thread effect and improve the quality and efficiency of treatment delivery. In some preexisting methods, other parameters of a treatment delivery system may be optimized, however, the pitch could not be adjusted during this process. Rather, a fixed pitch would be selected for the entire optimization process. If a different pitch is desired, the optimization process would be restarted from the beginning. Thus, the pitch is not optimized in preexisting methods.

The methods 200 and 300 illustrated herein are capable of optimizing the pitch as well as optimizing the beamlet weights. In other words, it is possible to optimize both the beamlet weights and the pitch without having to hold the one of these values at a fixed value throughout the entire optimization process. Instead, both the beamlet weight sinogram and the pitch can be adjusted during the optimization process (step 166). The pitch and the beamlet weights can be independently optimized by holding the other constant for a portion of the optimization process (166). However, it is not necessary to hold the pitch constant during the full optimization process (step 166). Furthermore, in some embodiments, both the pitch and the beamlet weights are optimized, while in other embodiments, only one of the pitch and the beamlet weights are optimized.

FIG. 6 illustrates a method 200 of carrying out the optimization process (step 166) of method 150 according to one embodiment. According to the method 200, the pitch of the treatment delivery system 11 is optimized (step 204). In some embodiments, the pitch is independently optimized by holding the value of beamlet weights constant while the pitch is optimized. The pitch can be optimized by the controller 72, which is capable of executing instructions to carry out any one of a variety of standard optimization techniques, including a linear model, a non-linear model, gradient optimization methods, and evolutionary methods. In some embodiments, an initial pitch can be used as a starting point and the controller 75 can execute instructions to the optimization module 100 to determine the optimal pitch closest to the initial pitch. The number of optimization iterations can vary. In some embodiments, the controller 75 can execute multiple iterations of optimization before it determines the optimal pitch. In other embodiments, a single optimization iteration is used before moving to the next step. In addition, in some embodiments, a user can instruct the controller 75 to carry out a predetermined number of optimization iterations. Alternatively, the user may view the pitch calculated after each iteration, and can manually stop the controller 75 from carrying out another iteration of optimization.

The method 200 also includes optimizing the modulation of the beamlet weights (step 208). More specifically, the controller 75 executes instructions to the optimization module 100 to carry out a process of modulating the beamlets 30A to achieve a desired dose (or prescribed dose). Recall that information regarding the modulation of the beamlet weights can be represented by a beamlet weight sinogram. Similar to the optimization of the pitch (step 204), the controller 75 can execute multiple iterations of the beamlet weight optimization (step 208). The number of iterations can vary and optimization of the beamlet weights can be terminated in a variety of ways, as described above. In some embodiments, the beamlet weights are independently optimized by holding the pitch constant while the beamlet weights are optimized.

In some embodiments, optimization of the pitch (step 204) and optimization of the beamlet weights (step 208) may occur sequentially, as distinct and separate cycles. For example, the pitch may be optimized (step 204) prior to the controller 75 optimizing the beamlet weight sinogram (step 208). In this case, the pitch may completely optimized prior to beginning optimization of the beamlet weights so that optimization of the beamlet weights can begin with an optimal pitch.

In other embodiments, optimization of the pitch (step 204) and optimization of beamlet weights (step 208) are executed simultaneously, as a combined alternating cycle. For example, in an alternating cycle, the controller 75 can alternate between executing instructions to optimize the pitch (step 204) and executing instructions to optimize the beamlet weights (step 208) until both the pitch and the beamlet weights are sufficiently optimized. In other words, one or more iteration of optimizing the beamlet weights (step 208) is interrupted by one or more iteration of optimizing the pitch (step 204). In this case, the pitch can be updated between every iteration or every few iterations of the beamlet weight optimization based on adjustments to the beamlet weight modulation.

For example, an optimization cycle may include a single iteration of the optimizing the beamlet weights (step 208) followed by a single iteration of optimizing of the pitch (step 204). This cycle may be repeated by returning to another single iteration of optimizing the beamlet weights (step 208) and repeatedly executing the cycle. The optimization cycle can include any number of iterations of optimization, and the iterations can occur in any order. For example, the cycle may include a series of two iterations of optimizing the pitch followed by a series of three iterations of optimizing the beamlet weights. In some embodiments the optimization process (step 166) is completed after one series of iterations, while in other embodiments the series can be repeated. Between each iteration of optimization, one or both of the pitch and the beamlet weights may be adjusted.

In some embodiments, optimization of the beamlet weights can be achieved by ignoring the helical path of the treatment delivery system 11 when determining the desired beamlet weights. Rather, the beamlet weights are determined by modeling the movement of the gantry 18 as a sequence of circular trajectories that are separated by small increments of linear movement of the couch 82 position. This geometry is referred to as "axial geometry." In other words, rather than using helical geometry to optimize and modulate the beamlet weights, axial geometry is used. This effectively decouples the beamlet weights from the optimization of the pitch, which uses helical geometry. FIGS. 7 and 8 illustrate a method 300 of executing the optimization process (step 166) of method 150 by utilizing a combination of different geometries to optimize the pitch and the beamlet weights.

Once both the pitch and the beamlet weights are optimized, the controller executes instructions 74 to calculate the dose and determine a treatment plan (step 212). In some embodiments, the controller 75 executes instructions to calculate the dose after each iteration of optimizing the pitch (step 204) or after each iteration of optimizing the beamlet weights (step 208), or both. The controller 75 can compare the calculated dose with the desired dose or dose volume histogram to identify whether the pitch and/or beamlet weights are sufficient to achieve the desired dose. In addition, the controller 75 can determine whether the calculated dose meets the clinical objectives and requirements of the prioritization module 99. When the calculated dose meets the clinical objectives, the controller 75 can determine a treatment plan based on the optimized pitch and the optimized beamlet weights (step 212). Once the controller 75 determines a treatment plan, the controller 75 can output the treatment plan (step 216).

FIG. 7 illustrates another method 300 of carrying out the optimization process (166) of method 150. The method 300 begins with inputting initial parameters as a starting point (step 304). For example, an initial pitch and an initial beamlet weight sinogram can be inputted by a user. The initial parameters can also be inputted by the controller 75 based on information already inputted into the other modules 95, 97, and 99, or based on a predetermined chart saved in the memory 81. In the illustrated embodiment, the initial sinogram accounts for the beamlets 30A having equal weights. In other embodiments, the initial sinogram represents a different set of beamlet weights. In addition to the initial pitch and the initial sinogram, any clinical objectives that were not previously inputted into any of the modules 95, 97, 99, and 100 can be added (step 304). For example, a desired dose and a set of clinical constraints limiting the amount of radiation a particular region or structure may receive may be inputted.

The controller 75 then executes instructions to calculate the dose resulting from the input parameters (step 308a). In the illustrated embodiment, the dose is calculated based on the initial pitch and the initial beamlet weight sinogram. The controller 75 can compare the calculated dose to the objectives (step 308a). For example, the controller 75 can determine how close the calculated dose is to the desired dose or the desired dose volume histogram. The controller 75 can also determine whether the calculated dose falls within the scope of the constraints. In some embodiments steps 304 and 308a are omitted from the method 300.

The controller 75 then executes instructions to the optimization module 100 to carry out an optimization procedure to adjust the beamlet weights (step 312). More specifically, the controller 75 optimizes the beamlet weights by executing multiple iterations of beamlet weight modulation to achieve the desired dose. During each iteration of optimization, the beamlet weights are adjusted from the previous iteration. During the first iteration, the beamlet weights are adjusted from the initial sinogram, which accounts for the beamlets 30A having equal beamlet weights. In the illustrated embodiment, optimization of the beamlet weights 30A is based on axial geometry, in which the gantry 18 is modeled as moving through a series of circular trajectories that are separated by small increments of the couch 82 position. In other words, optimization of the beamlets is calculated based on a discrete set of circular rotations of the gantry 18 that are separated by discrete linear translations of the couch 82. On the other hand, dose is calculated using helical geometry, which is modeled as a continuous rotation of the gantry 18 combined with a continuous translation of the couch 82 to form a helix. Accordingly, the beamlet weight sinogram is translated from axial geometry to helical geometry (step 316) prior to calculating the dose.

The controller 75 then executes instructions to calculate the dose based on the adjusted beamlet weights determined during optimization (step 308b). In some embodiments, the dose is calculated after each iteration of optimizing the beamlet weights. In this case, the beamlet weight sinogram is translated to helical geometry between each iteration of optimizing the beamlet weights. In other embodiments, the dose is only calculated every few iterations of optimization. In this case, the beamlet weight sinogram may be translated to helical geometry only when calculating the dose. For example, pitch optimization could be performed whenever the optimization module 100 performs a full dose iteration, while all approximate dose iterations could operate entirely on the axial geometry.

The method 300 also includes optimizing the pitch of the treatment delivery system 11 (step 320). The controller 75 executes instructions to the optimization module 100 to determine the optimal pitch closest to the initial pitch input. The controller 75 can execute multiple iterations of optimizing the pitch before terminating the optimization process. In some embodiment, the beamlet weights are adjusted prior to the pitch being adjusted, however, in other embodiments, the pitch is adjusted first. Also, as discussed above with respect to method 200, beamlet weight optimization and pitch optimization may occur simultaneously, for example, using an alternating cycle. Alternatively, beamlet weight optimization and pitch optimization may be executed as a distinct and separate cycles that occur sequentially. In addition, the number of iterations can vary and optimization of the beamlet weights and the pitch can be terminated in a variety of ways, as described above with respect to method 200.

The controller 75 may then execute instructions to calculate the dose based on the adjusted pitch determined during optimization (step 308c). As described with respect to step 308b, the dose may be calculated between some iterations of optimization but not others. Furthermore, in some embodiments, the pitch is translated to a new geometry before calculating dose and determining a treatment plan (see step 324 in FIG. 8). For example, the pitch may be translated to a different helical geometry.

Although the method 300 is illustrated with the pitch optimized using helical geometry and the beamlet weights being optimized using axial geometry, a variety of other geometries can be used. For example, in some embodiment, the pitch is optimized using a first helical geometry and the beamlet weights are optimized using a second helical geometry that is different than the first geometry. In this embodiment, the pitch and the beamlet weights are then translated to the same geometry when determining a treatment plan. This can be done in a variety of ways. For example, the pitch may be translated from the first geometry to the second geometry, the beamlet weights may be translated from the second geometry to the first geometry, or the pitch and the beamlet weights may both be translated to a third geometry. In other embodiments, the pitch is optimized using a first helical geometry, the beamlet weights are optimized using a first axial geometry; and then both the pitch and the beamlet weights are translated to a third geometry. The geometry of the pitch and the beamlet weights can be translated between each optimization cycle or only after the completion of the optimization process.

In some embodiments, the optimized pitch, the optimized beamlet weights, or the treatment plan may include varying geometries. For example, the optimized pitch may be a varied pitch, such that the pitch uses a different geometry at different portions of the treatment plan. In other words, the pitch may have a first helical geometry during a first portion of the treatment plan and may have a second helical geometry during a second portion of the treatment plan.

FIG. 8 illustrates some of the different optimization cycles that are available. A single iteration of pitch optimization is represented by Cycle A (step 320). Cycle A includes an optional step (step 324) of translating the pitch to a new geometry. When different geometries are used to calculate the beamlet weights or to calculate dose and determine a treatment plan, it may be desirable to translate the geometry of the pitch to either the geometry of the beamlet weights or the geometry being used to calculate dose and determine a treatment plan. However, this step is not always needed. A single iteration of beamlet weight optimization is represented by cycle B (step 312). Similar to Cycle A, Cycle B includes an optional step (step 316) of translating the beamlet weights to a new geometry. The beamlet weights may be translated to the geometry of the optimized pitch or to another geometry being used to calculate dose and determine a treatment plan. An iteration of optimizing both pitch and beamlet weights combines Cycle A and Cycle B. This can be referred to as an AB Cycle.

Also, as previously mentioned, dose calculation (step 308) may not be executed every time the pitch or the beamlet weights are optimized. Accordingly, Cycle C represents optimization of the pitch (step 320) without calculating the dose (step 308) afterwards. Cycle C will also generally not include translating the pitch to a new geometry (step 324). However, in some embodiments, the pitch may be translated to a new geometry even when the dose is not being calculated. Cycle D represents optimization of the beamlet weights (step 316) without calculating dose (step 308) afterwards. Like Cycle C, Cycle D will generally not include the step (step 316) of translating the beamlet weights to a new geometry, but this step (step 316) may be included in some instances. The controller 75 determines the treatment plan when the dose is calculated for the final time and the dose meets the clinical objectives. The controller 75 can use the most recent optimized pitch and optimized beamlet weights to determine the treatment plan.

The method 300 can be executed by combining a series of optimization cycles together, similar to those discussed with respect to method 200. Cycles A-D can be combined into various series to fulfill the complete optimization process (step 166) of method 150. For example, the optimization process (step 166) may be executed using method 300 according to the following series: BADBCA—repeat twice. In this embodiment, the pitch and the beamlet weights are optimized simultaneously according to an alternating series. The controller can also execute instructions to the optimization module 100 to follow a series that optimizes pitch and beamlet weights as separate cycles. For example, the following series may be followed: CCACCA-DDBDDB. In this embodiment, the pitch is fully optimized prior to optimizing the beamlet weight sinogram. FIG. 7 also indicates, through the "optional repeat" notations some of the ways in which the optimization cycles may be repeated.

Additional steps beyond those described in methods 200 and 300 may be included in the optimization process (step 166). For example, the controller 75 may execute instructions to apply a scaling factor to the beamlet weights. This allows the dose to be scaled up or down to achieve the desired dose or the primary dose volume histogram point. Additionally, the controller 75 may execute instructions to place a limit on the degree to which the beamlet weights vary from one another. The degree of variation between the weights of the beamlets 30A is referred to as the modulation factor. When the beamlet weights begin to vary too much (e.g., one leaf 66 is open for a very long amount of the time relative to another leaf 66), the controller 75 can limit (or clamp) the degree to which the beamlet weights differ. In one embodiment, the limit is determined by taking the average of the beamlet weights and multiplying it by a user selected modulation factor (e.g., 2.0). This will become the maximum possible beamlet weight. When a beamlet weight goes beyond the maximum, the controller can execute instructions to reduce that beamlet weight to the maximum value.

Once the beamlet weight sinogram and the pitch are optimized (step 166), the controller 75 executes to complete the method 150 by carrying out the fractionation process (step 170). As described herein, the methods 200, 300 are primarily used during the treatment planning phase to help determine an optimal treatment plan. In other embodiments, the methods 200, 300 may be carried out during treatment, so that the pitch and the beamlet weights of the treatment delivery system 11 can be adjusted mid treatment.

Various features and advantages of the invention are set forth in the following claims.

What is claimed is:

1. A method of selecting a radiation therapy treatment plan for a patient, the treatment plan implemented through a radiation delivery system including a gantry configured to rotate around a couch, the couch movable in a linear direction relative to the gantry, the movement of the couch and the gantry creating a helical delivery path having a pitch, and a radiation module coupled to the gantry and configured to deliver a radiation beam, the beam having a beam weight corresponding to a radiation fluence, the method comprising:

receiving, by a controller, an objective including at least one from a list including a desired dose, a desired dose distribution, and a dose constraint;

optimizing, by the controller, the pitch based on the objective to obtain an optimized pitch;

optimizing, by the controller, the beam weight based on the objective to obtain an optimized beam weight;

determining, by the controller, based on the optimized pitch and the optimized beam weight at least one from the following list including a treatment plan and a dose; and outputting, by the controller, the at least one of the treatment plan and the dose.

2. The method of claim 1, wherein optimizing the pitch includes optimizing the pitch using a first geometry, and wherein optimizing the beam weight includes optimizing the beam weight using a second geometry.

3. The method of claim 2, wherein the first geometry is a helical geometry and the second geometry is an axial geometry.

4. The method of claim 2, wherein the first geometry is a helical geometry and the second geometry is a helical geometry that is different from the first geometry.

5. The method of claim 2, further including translating the beam weight from the second geometry to the first geometry prior to determining at least one of the treatment plan and the dose.

6. The method of claim 1, wherein optimizing the beam weight includes optimizing the beam weight using axial geometry, wherein axial geometry is modeled as a sequence of discrete circular rotations of the radiation module, separated by incremental linear movements of the couch.

7. The method of claim 1, wherein the optimized pitch is a variable pitch such that optimized pitch corresponds to different geometries at different stages of the treatment plan.

8. The method of claim 1, wherein the controller optimizes the pitch and the beam weight sequentially such that one of the pitch and the beam weight is fully optimized prior to beginning optimization of the other one of the pitch and the beam weight.

9. The method of claim 1, wherein the controller optimizes the pitch and the beam weight simultaneously such that the controller alternates between executing instructions to optimize the pitch and executing instructions to optimize the beam weight.

10. The method of claim 1, wherein the radiation module includes a modulation device capable of shaping the beam into a plurality of beamlets, each beamlet having a beamlet weight, and wherein the controller optimizes the beam weight by optimizing the beamlet weights.

11. The method of claim 10, wherein the plurality of beamlet weights is represented as a beamlet weight sinogram, and wherein optimizing the beamlet weights includes optimizing the beamlet weight sinogram.

12. The method of claim 1, wherein the controller optimizes at least one of the pitch and the beam weight by executing a plurality of optimization iterations.

13. The method of claim 1, wherein the controller receives as a user input an initial pitch, and the pitch is optimized to obtain an optimal pitch close to the initial pitch.

14. A radiation therapy treatment system, comprising:

a gantry having an aperture;

a couch configured to support a patient, the couch movable in a linear direction within the aperture;

a radiation module coupled to the gantry and rotatable around the couch, the radiation module configured to deliver a radiation beam toward the patient, the radiation beam having a beam weight corresponding to a radiation fluence, wherein the linear movement of the couch and the rotation of the radiation module create a helical path of radiation delivery, the helical path having a pitch; and a computer in communication with the gantry, the radiation module, and the couch, the computer including a controller configured to
  optimize the pitch of the radiation module based on clinical objectives for the patient,
  optimize the beam weight of the radiation beam based on clinical objectives for the patient,
  determine at least one of a treatment plan and a dose based on the optimized pitch and the optimized beam weight, and
  output the at least one of the treatment plan and the dose.

15. The radiation therapy treatment system of claim 14, wherein the controller is configured to optimize the pitch using a first geometry and is configured to optimize the beam weight using a second geometry.

16. The radiation therapy treatment system of claim 15, wherein the second geometry is an axial geometry that is modeled as a sequence of discrete circular rotations of the radiation module, separated by incremental linear movements of the couch.

17. The radiation therapy treatment system of claim 15, wherein the first geometry is a helical geometry and the second geometry is a helical geometry that is different than the first geometry.

18. The radiation therapy treatment system of claim 15, wherein the controller is further configured to translate the beam weight from the second geometry to the first geometry.

19. The radiation therapy treatment system of claim 14, wherein the optimized pitch is a variable pitch such that optimized pitch corresponds to different geometries at different stages of the treatment plan.

20. The radiation therapy treatment system of claim 14, wherein the radiation module includes a modulation device capable of shaping the beam into a plurality of beamlets, each beamlet having a beamlet weight, and wherein the controller is configured to optimize the beamlet weights.

21. The radiation therapy treatment system of claim 20, wherein the modulation device includes a multi-leaf collimator having a plurality of leaves each configured to selectively block and selectively expose one of the plurality of beamlets, the beamlet weight corresponding to the amount of time a beamlet is exposed.

22. The radiation therapy treatment system of claim 20, wherein the beamlet weights are represented as a sinogram, and wherein the controller is configured to optimize the beam weight by optimizing the sinogram.

23. The radiation therapy treatment system of claim 14, wherein the controller is further configured to optimize the pitch and the beam weight simultaneously using an alternating series of optimization cycles.

24. The radiation therapy treatment system of claim 14, wherein the controller is further configured to optimize the pitch and the beam weight sequentially such that one of the pitch and the beam weight is fully optimized prior to the controller beginning optimization of the other of the pitch and the beam weight.

25. A method of selecting a radiation therapy treatment plan for a patient, the treatment plan implemented through a radiation delivery system including a gantry configured to rotate around a couch, the couch movable in a linear direction relative to the gantry, and a radiation module coupled to the gantry and configured to deliver a radiation beam, the beam having a beam weight corresponding to a radiation fluence, the method comprising:
  receiving, by a controller, an objective including at least one from a list including a desired dose, a desired dose distribution, and a dose constraint;
  receiving, by the controller, a first pitch and a first beam weight;
  adjusting, by the controller, the first pitch using a first geometry and the objective to determine an adjusted pitch;
  adjusting, by the controller, the first beam weight using a second geometry and the objective to determine an adjusted beam weight;
  translating, by the controller, the adjusted beam weight from the second geometry to the first geometry; and
  calculating, by the controller, an adjusted dose based on the adjusted pitch and the adjusted beam weight, the adjusted dose represented in the first geometry.

26. The method of claim 25, wherein the controller adjusts at least one of the pitch and the beam weight during treatment delivery to a patient.

27. The method of claim 25, wherein adjusting the first pitch occurs after adjusting the first beam weight.

28. The method of claim 25, wherein the beam includes a plurality of beamlets, each beamlet having a beamlet weight, and wherein adjusting the first beam weight includes adjusting a plurality of beamlet weights.

* * * * *